(12) United States Patent
Matta et al.

(10) Patent No.: US 9,119,610 B2
(45) Date of Patent: Sep. 1, 2015

(54) MEDICAL TABLE HAVING CONTROLLED MOVEMENT AND METHOD OF USE

(76) Inventors: Joel M. Matta, Toluca Lake, CA (US);
Stephen L. Hoel, Fremont, CA (US);
Steven R. Lamb, Diablo, CA (US)

(*) Notice: Subject to any disclaimer, the term of this patent is extended or adjusted under 35 U.S.C. 154(b) by 0 days.

(21) Appl. No.: 11/502,290

(22) Filed: Aug. 10, 2006

(65) Prior Publication Data

US 2007/0251011 A1     Nov. 1, 2007

Related U.S. Application Data

(60) Provisional application No. 60/707,080, filed on Aug. 10, 2005.

(51) Int. Cl.
| | |
|---|---|
| A47B 7/00 | (2006.01) |
| A61B 19/02 | (2006.01) |
| A61G 13/12 | (2006.01) |
| A61G 13/00 | (2006.01) |

(52) U.S. Cl.
CPC ........ *A61B 19/0248* (2013.01); *A61G 13/0036* (2013.01); *A61G 13/12* (2013.01); *A61G 13/123* (2013.01); *A61G 13/1205* (2013.01); *A61G 2203/12* (2013.01)

(58) Field of Classification Search
CPC . A61G 13/12; A61G 13/1205; A61G 13/123; A61G 13/1245
USPC ............ 5/624, 621, 619, 607, 610, 611, 602, 5/616, 608
See application file for complete search history.

(56) References Cited

U.S. PATENT DOCUMENTS

| | | | | |
|---|---|---|---|---|
| 4,143,652 | A | 3/1979 | Meier et al. | 128/20 |
| 4,373,709 | A | 2/1983 | Whitt | 269/328 |
| 4,428,571 | A | 1/1984 | Sugarman | 269/328 |
| 4,660,817 | A * | 4/1987 | Kowalski | 5/610 |
| 4,940,218 | A * | 7/1990 | Akcelrod | 5/621 |
| 5,528,782 | A * | 6/1996 | Pfeuffer et al. | 5/611 |
| 5,806,117 | A * | 9/1998 | Gotfried | 5/624 |
| 6,012,456 | A | 1/2000 | Schuerch | 128/869 |
| 6,295,671 | B1 | 10/2001 | Reesby et al. | 5/600 |
| 6,315,718 | B1 | 11/2001 | Sharratt | 600/228 |
| 6,640,363 | B1 * | 11/2003 | Pattee et al. | 5/601 |
| 7,824,353 | B2 * | 11/2010 | Matta | 602/35 |
| 2003/0145383 | A1 * | 8/2003 | Schwaegerle | 5/610 |
| 2004/0133979 | A1 * | 7/2004 | Newkirk et al. | 5/600 |
| 2006/0064103 | A1 | 3/2006 | Matta | 606/86 |

FOREIGN PATENT DOCUMENTS

EP      0 923 922 A2     6/1999 ............ A61G 13/02

* cited by examiner

*Primary Examiner* — Robert G Santos
*Assistant Examiner* — David E Sosnowski
(74) *Attorney, Agent, or Firm* — Theodore J. Bielen, Jr.

(57) ABSTRACT

A medical table provides the functionality needed for hip and knee arthroplasty at a cost that is acceptable for smaller patient care centers. Such a table can use a sliding mechanism to maintain traction during positioning of a patient's leg. The table also can utilize a knee arthroplasty attachment to provide for precise knee positioning, such as by using a sliding assembly attached to a spar of the table. The table can include a pair of actuators providing for both lateral tilt and trendelenburg motions, which reduces the complexity from previous tables. The table also can include a removable power/control module, which allows for quick and easy replacement of damaged components.

11 Claims, 17 Drawing Sheets

MEDICAL TABLE HAVING CONTROLLED MOVEMENT AND METHOD OF USE

This application claims the benefit of U.S. Provisional Application No. 60/707,080, filed Aug. 10, 2005, which is incorporated herein by reference.

TECHNICAL FIELD OF THE INVENTION

The present invention relates to medical tables and medical supports, particularly those useful for supporting a patient during a procedure such as hip or knee replacement.

BACKGROUND

Recent advances in surgery focus on minimally invasive techniques, which utilize smaller and/or a fewer number of incisions, and can eliminate the need in previous techniques to detach or sever muscular tissue. For example, minimally invasive hip replacement surgery utilizes entry at the anterior of the leg of a patient. This point of entry allows a surgeon to perform a hip replacement procedure while only making a single incision of about four inches in length, rather than multiple incisions or incisions of ten inches in length as in prior procedures. Further, muscles within the leg are not damaged through detachment or severing in these procedures, resulting in a much faster recovery time. These procedures still require access to the acetabulum, which must be reamed before insertion of the prosthesis. Further, proper manipulation and positioning of the femur is essential in carrying out the anterior approach hip replacement surgery.

DETAILED DESCRIPTION

Figure 1:
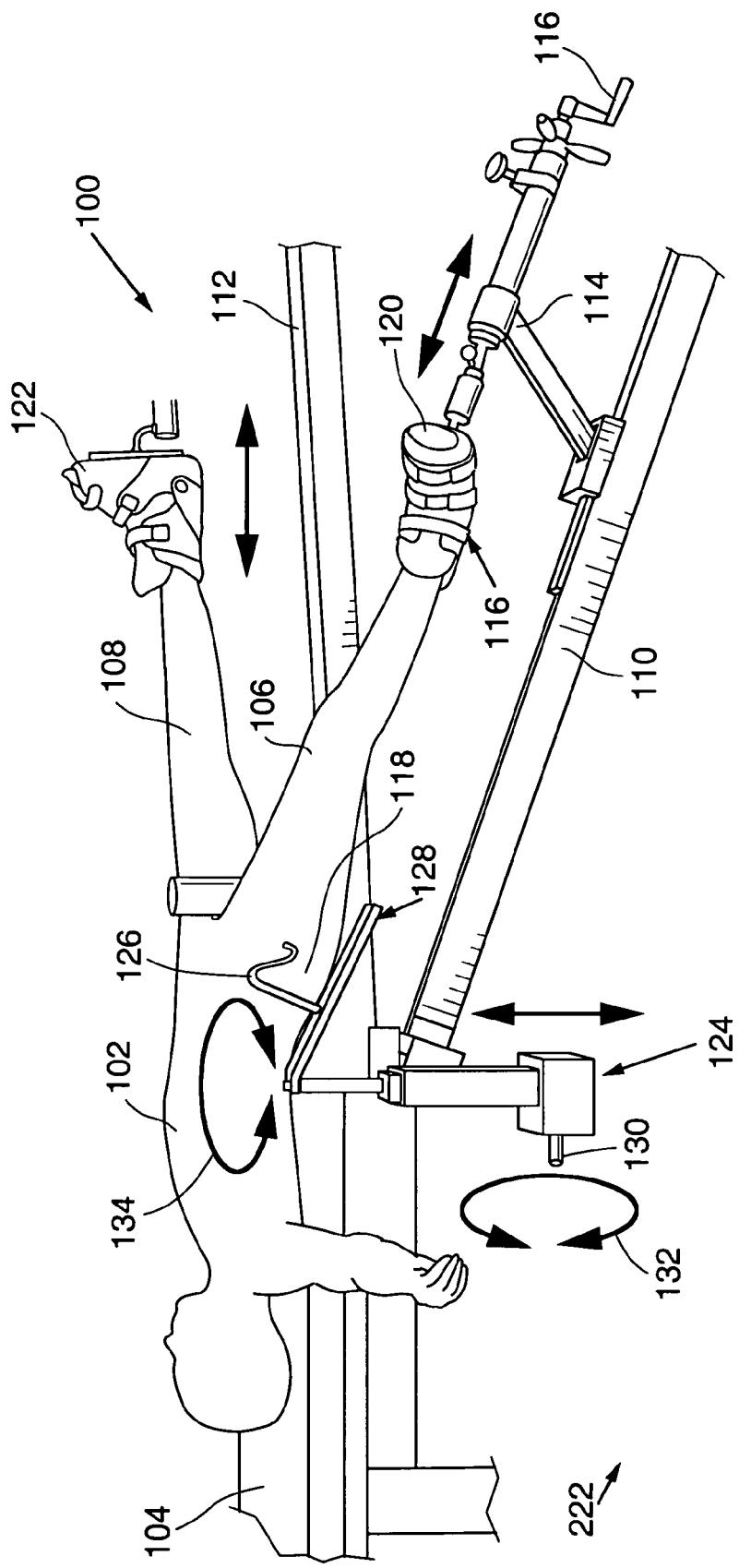
FIG. 1 is a perspective view of a prior art medical table illustrating a patient positioned on the table.

Systems and methods in accordance with various embodiments of the present invention can overcome deficiencies in existing medical tables and support structures for procedures such as hip and knee arthroplasty. The present assignee has previously made great strides in the field of medical tables for such procedures, producing tables such as the PROfx™ Orthopedic Surgical Table available from OSI of Union City, Calif. An illustration of such a table 100 is shown in FIG. 1. A patient 102 undergoing such a surgery typically will be anesthetized for surgery then placed on the surgical table 100. The back of the patient will be placed on a platform portion 104 of the table, with the legs 106, 108 of the patient being placed over the spars 110, 112 of the table. Each spar has a traction system 114 (not shown for the left leg) for receiving a foot of the patient and holding that foot in a desired position. The traction system can have a traction setting mechanism 116 for applying a desired amount of force on the foot of the patient. The hip 118 of the patient is placed adjacent to a pivot connection between the platform portion 104 and the spars 110, 112 in order to allow the legs of the patient to be moved into a position appropriate for surgery, such as for anterior approach hip surgery. In this figure, the patient is positioned for surgery on the hip associated with right leg 106. Traction boots 120, 122 can be used to ensure traction via the traction system. A manual surgical table jack 124 can be used to raise and lower a femoral support hook 126, connected to the jack by an angled bracket member 128. The raising and lowering of the jack 124 can be accomplished via the rotation or a rotatable shaft 130, the motion of which is indicated by directional arrow 132. The angled bracket 128 is also capable of rotating relative to the jack 124, such that the surgeon performing the surgery can rotate the hook into and out of position, providing complete control of the positioning of the support 128 relative to the femur within the right leg 106, the end portion of the hook being shaped to receive and support the femur during the procedure. An appropriate hook is described in pending U.S. patent application Ser. No. 10/930,809, entitled "Surgical Support for Femur," to Joel M. Matta, filed Sep. 1, 2004, published Mar. 23, 2006 as U.S. Publication No. 2006/0064103, which is hereby incorporated herein by reference. There can be a hook and corresponding components on each side of the table, one for each leg, in order to allow for operation on either side of the patient.

In operation, the surgeon places a base portion of the support hook 126 into an appropriate opening on the angled bracket 128. The bracket has a plurality of openings for receiving the base portion, in order to position the receiving end of the hook at an appropriate distance from the femur to be supported. At the proper time after an incision is made in the patient, the hook 126 on the appropriate side can be swung into position in the wound at the hip region of the patient, and can be positioned to support the femur. The surgeon (or an assistant) then can manually adjust the jack 124 to properly angle and support the femur such that the surgeon can gain unrestricted access to the acetabulum and other portions of the hip in order to accomplish an artificial hip replacement for the patient. When the support of the femur is no longer needed, the support including the hook can be lowered using the jack, and then swung from the wound in the patient and moved outwardly by the rotation of bracket 128 relative to the jack 124, as shown by directional arrow 134. The hook 128 then can be removed or left in this position as surgery progresses and is finished.

While such a table offers extreme flexibility, it has a disadvantage for certain users of having a relatively high cost (due in part to the amount of flexibility and functionality). While such cost might be acceptable for a trauma center, which may need or desire all the functionality, the cost might be excessive for a doctor doing only hip and/or knee replacements. It therefore is desirable to provide a table that provides the functionality needed for hip/knee arthroplasty, but comes with a more reasonable price point. It also is desirable to build on the functionality of the table of FIG. 1 to provide an even more user-friendly experience.

Figure 2:
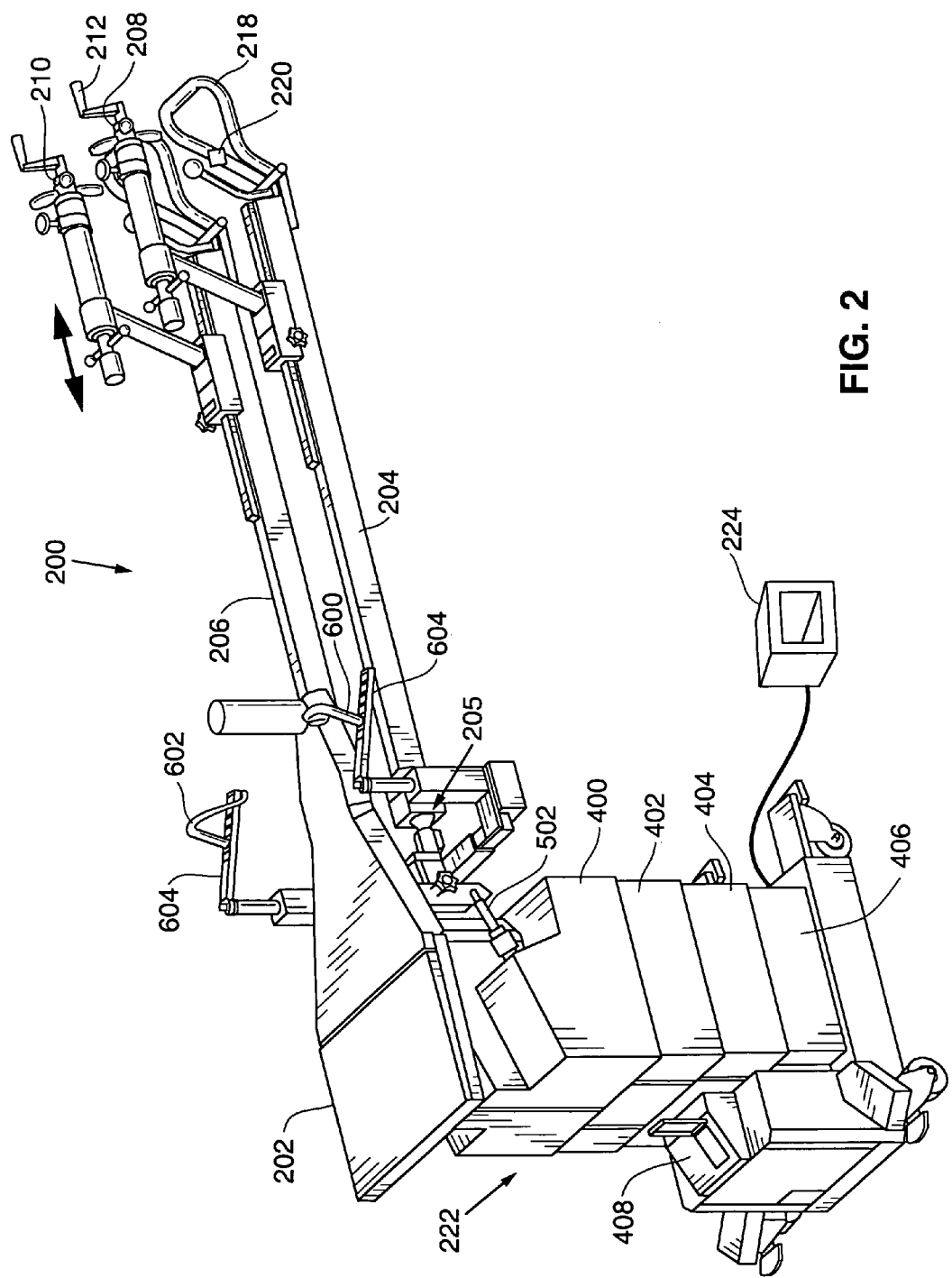
FIG. 2 is a perspective view of an embodiment of a medical table.
Figure 3:
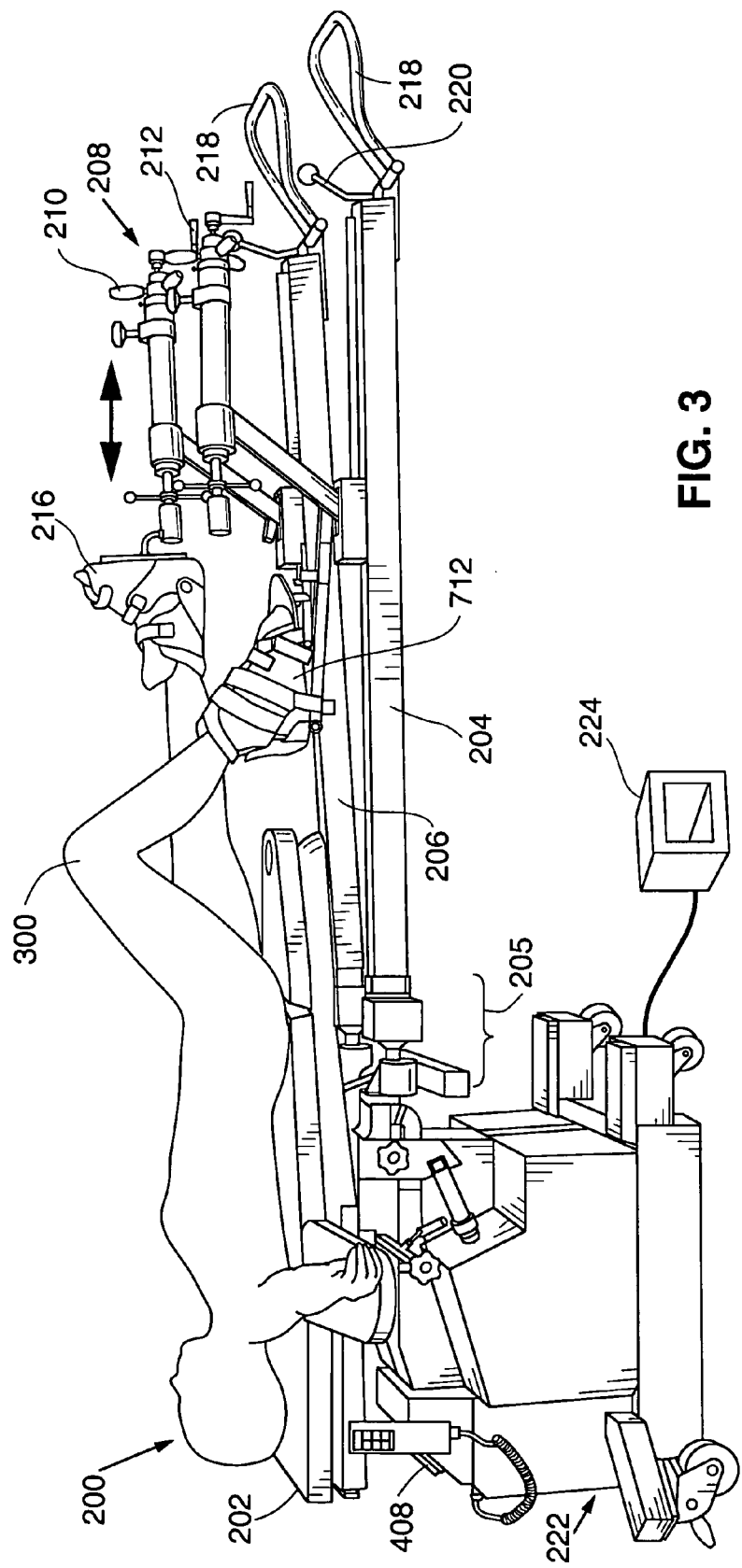
FIG. 3 is a perspective view of the medical table of FIG. 2, with a patient thereon.

Attempting to meet many of these desires, FIGS. 2 and 3 show a surgical table 200 in accordance with one embodiment. Features of the exemplary table can be found on the Hana™ Hip and Knee Arthroplasty Table available from OSI, Inc., 30031 Ahern Ave., Union City, Calif. 94587. This table provides the functionality needed for hip and knee arthroplasty, and can be produced at a cost that is acceptable for smaller patient care centers. The table offers solid stability and excellent rigidity, supporting patients up to 450 lb in one embodiment. The table also can have a low profile for easy patient transfer, and can be lowered to a height of approximately 28 inches or raised to a height of 48 inches. With its unique ability to position the leg, the table enables the surgeon to replace the hip through a single incision, anterior approach without detachment of muscle from the pelvis or femur. The table allows hyperextension, abduction, adduction, and external rotation of the hip for femoral component placement, which includes position options not possible with many conventional tables. The lack of disturbance to the lateral and posterior soft tissues provides immediate stability of the hip after surgery. Such a table is ideal for orthopedic trauma and minimally invasive orthopedic procedures. The table can include a remote control unit, such as a hand pendant, as well as auxiliary controls to provide for maximum ease of use during a procedure. These controls provide for extensive maneuverability, aiding the surgeon in articulation of the lower extremities.

As discussed above, such a table enables a surgeon to use a minimally invasive anterior approach requiring only a single incision. Such an approach does not require the cutting of muscle, but separates the muscle in a natural cleavage. The entire surgical procedure can take only on the order of hours, and patients often walk hours later and can go home next day. The table provides sufficient femoral support, with the leg in traction and externally rotated, that the femur is perfectly well stabilized to allow the surgeon to go through incision to do femoral component.

As seen in the figure, table 200 includes a platform portion 202 for receiving the back of a patient (as shown in FIG. 3), and spars 204, 206 for positioning the legs of the patient. Portions of the table such as the platform and spars can be formed of a radiolucent material such as a carbon fiber material. When combined with a 35 inch radiolucent cantilever top and radiolucent leg spars in one embodiment, such construction provides for extensive imaging capability for uninterrupted imaging from head to toe of a patient. The table also can allow for unrestricted C-arm access for x-ray imaging. A carbon fiber top and carbon fiber radiolucent leg spars can be positioned for unobstructed imaging of a patient's legs, hips, and pelvis while maintaining traction. The spars also can have a trapezoidal shape in cross-section, in order to prevent shadows during imaging.

Figure 4:
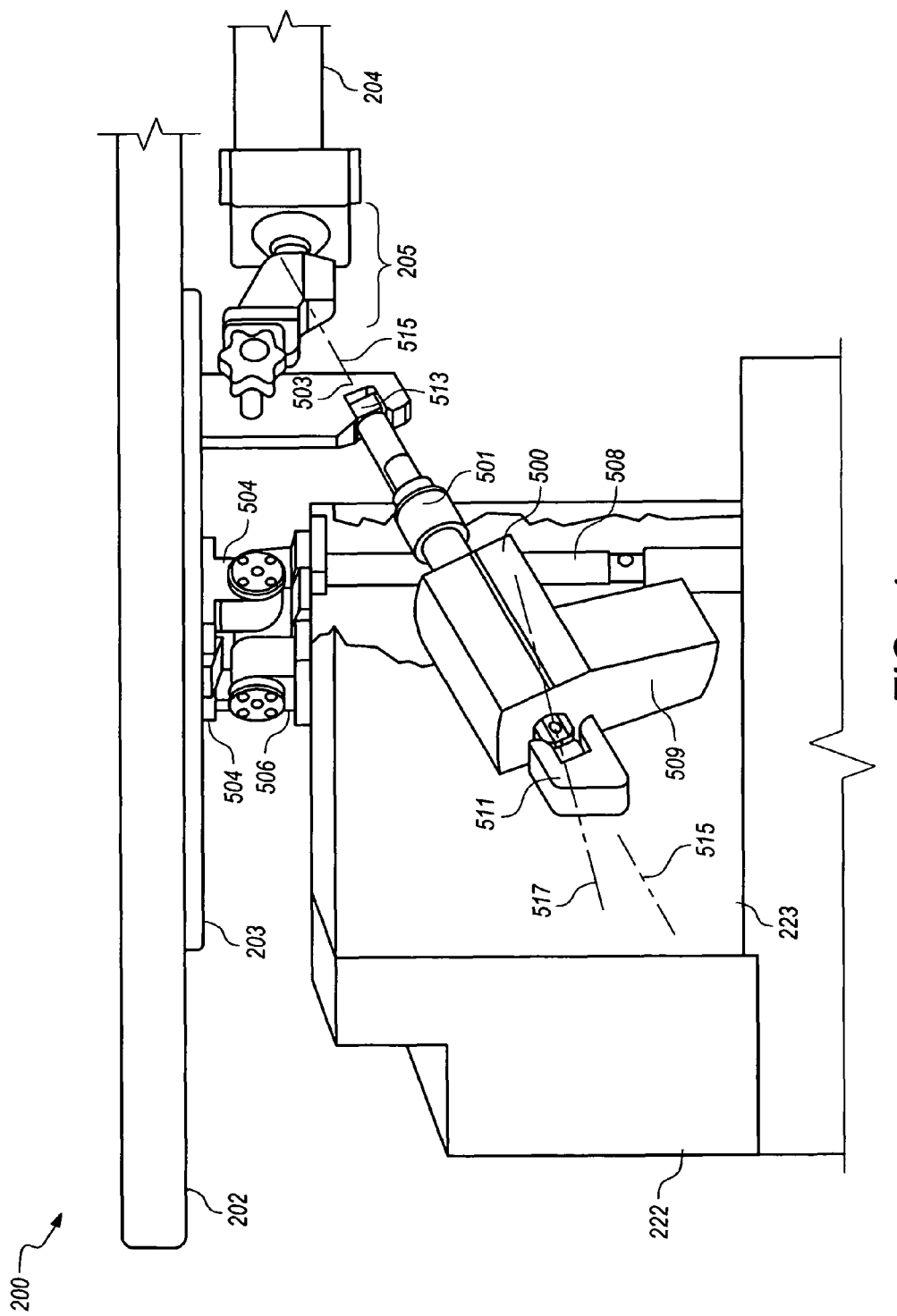
FIG. 4 is a side perspective view of a portion of the head end of the medical table of FIG. 2.

Both platform 202 and spars 204, 206 are supported by a plate 203 best shown in FIG. 4. FIG. 3 shows a patient 300 positioned on the table 200 for knee arthroplasty. Reference numbers are carried over where appropriate between figures for simplicity. The spars 204, 206 in one embodiment utilize a spherical spatial positioning system including a ball-joint style pivot connection 205 that provides for complex movement of the spars. Only the joint 205 for spar 204 is visible in FIG. 2, however a similar joint 205 is provided for spar 206. Each spar has a traction system 208, 210 for receiving a foot of the patient and holding that foot in a desired position. The traction system can have a traction setting mechanism 212 for applying a desired amount of force on the foot of the patient. Each foot can be received by a respective traction boot 214, 216 attached to one of the traction systems, allowing for precise control of patient position, manipulation, and traction. Each traction setting mechanism can be used to direct the respective boot toward or away from the platform portion 202, in order to adjust for leg length and to apply the appropriate supporting force.

The hip of the patient can be placed adjacent to a pivot connection 205 between the platform portion 202 and the spars 204, 206 in order to allow the legs of the patient to be moved into a position appropriate for surgery. Each spar can include a handle 218 allowing the surgeon or assistant to easily position the respective spar, and a release mechanism 220 that can be released to allow movement of the spar and tightened to lock the spar into place. The spars can provide for both horizontal (i.e. adduction and abduction) and vertical adjustment of the foot position, made possible, in part, by a rotary joint such as a ball joint (not shown) connecting each spar 204, 206 to the base portion 222.

The spars are cantilevered off the base portion 222, which includes an appropriate device for raising and lowering the table as known in the art. Referring to FIG. 4, in one embodiment a column 508 in the base 222 is coupled via other components (discussed below) to the plate 203 supporting the platform 202. Column 508 works with a bearing and slider mechanism to provide vertical motion via an electric actuator, thereby allowing the surgeon to raise and/or lower the entire working portion of the table, including the spars 204, 206. A foot pedal 224 can be provided that allows the surgeon to control the position of the table as needed. Methods for using a foot pedal with a linear actuator are well known in the art and will not be discussed herein in detail. As shown in FIG. 4, the base portion can include a number of telescoping members 400, 402, 404, 406 allowing the height of the base portion to be adjusted as necessary, such as by the surgeon activating the foot pedal, or through use of a control panel 408 on the base portion that can. This control panel can be fixed to the base station or can be removable to act as a remote control mechanism.

The plate 203 supporting platform 202 is coupled to the base 222 by a pair of actuators 500 (one of which is obscured in the drawings) positioned on opposite sides of the table. The actuators 500 can be used to provide for lateral tilt in both directions, as well as trendelenburg and reverse trendelenburg motions. In the illustrated embodiment, each actuator 500 has a motor 509 and an extendable member 501 of the type shown in FIGS. 4 and 11A-11D, but could, alternatively, utilize gears or lever assemblies as needed. Each extendable member 501 is mounted at one end via a coupling 511 to an interior portion of the base housing 223 (which is mounted within the upper tier 400 of base 222 (FIG. 2)), and has a coupling 513 at its other end connected to a support 503 suspended from plate 203. Each actuator 500 is pivotable about two orthogonal axes, 515 and 517, preferably at the coupling 511 between the member 501 and the base 222, as shown, to prevent binding of the actuator during table movement. Referring again to FIG. 4, additional freedom of movement is provided by a universal joint coupling the housing portion 223 to the plate 203. The universal joint is formed with a pivot 504 having a pivot axis transverse to the longitudinal axis of the table, and pivot 506 having a pivot axis parallel to the longitudinal axis of the table. When the table is moved into a lateral tilt (FIGS. 11B and 11C), the plate 203 pivots about the axis of pivot 506. When the table is moved into a trendelenburg position (FIG. 11D), the plate 203 pivots about the axis of pivot 506.

Figure 11A:
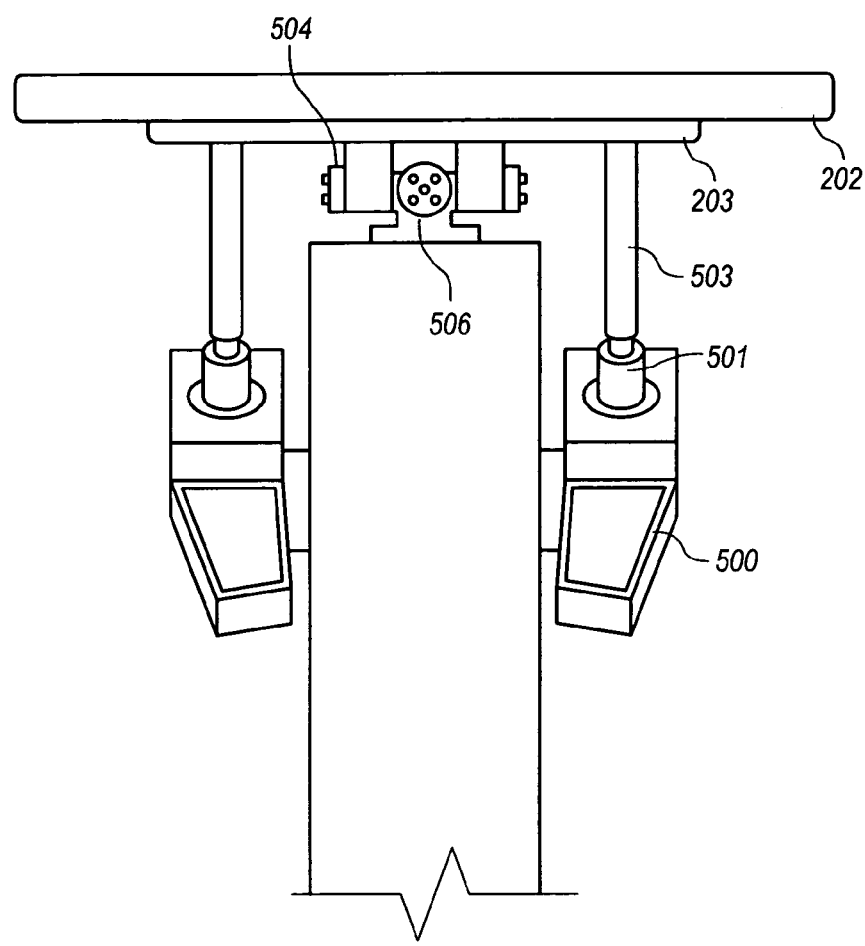
FIG. 11A is a front elevation view showing the platform in the level position.
Figure 11B:
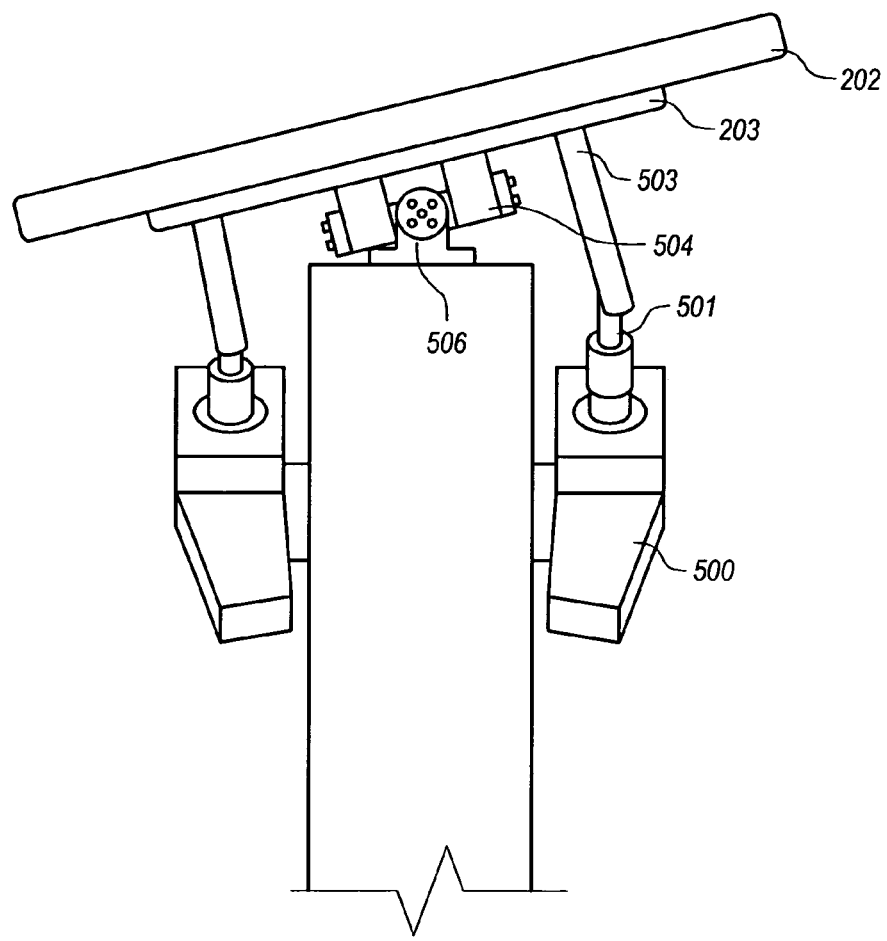
FIG. 11B is similar to FIG. 11A and shows the platform in a lateral tilt position.
Figure 11C:
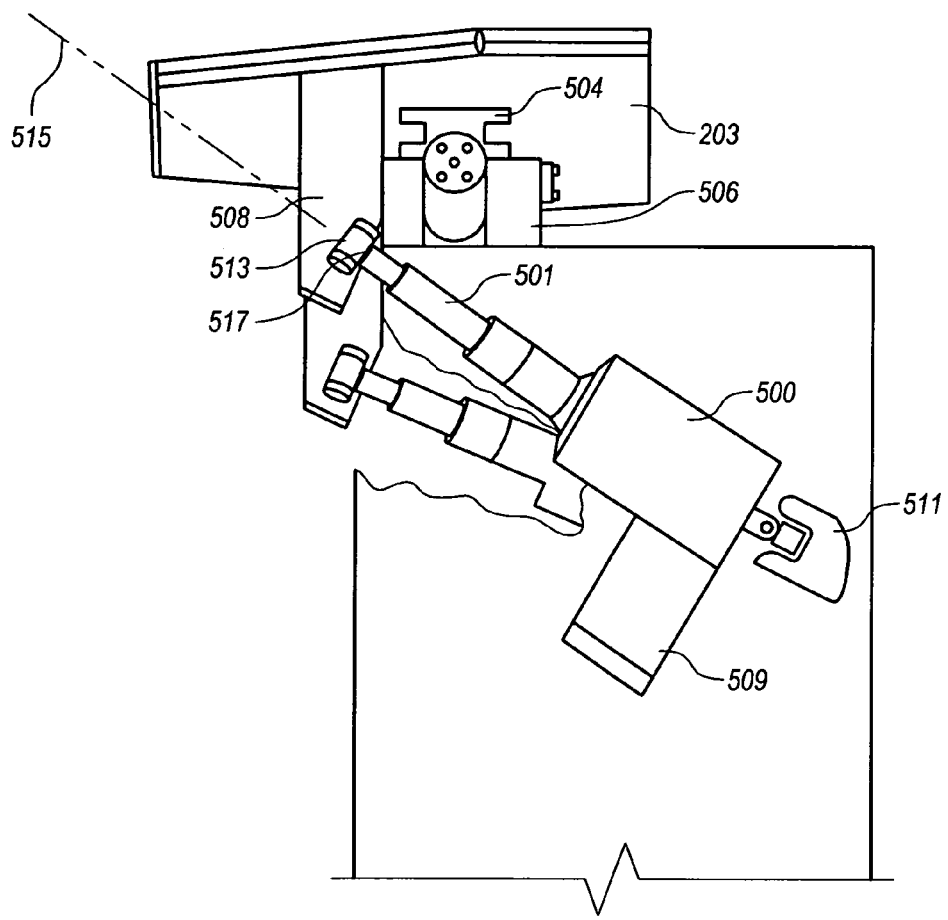
FIG. 11C is a side view showing the plate in the lateral tilt position shown in FIG. 11C. Here the platform is not shown for clarity.
Figure 11D:
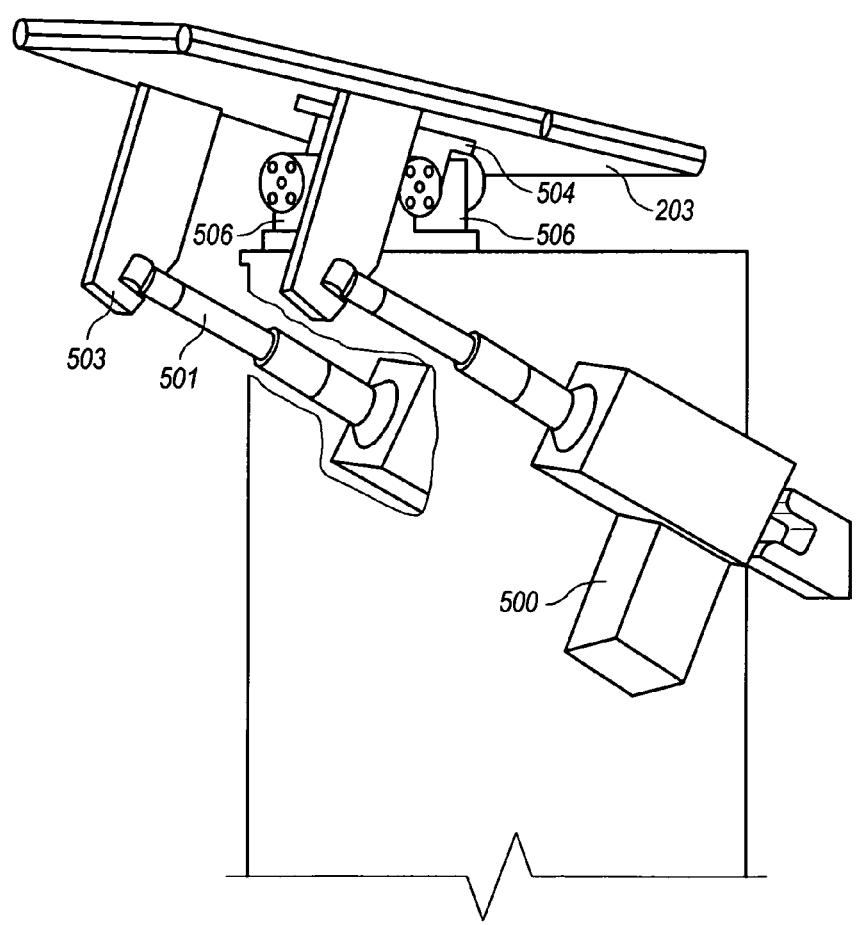
FIG. 11D is a side perspective view showing the plate a longitudinal tilt position. Here the platform is not shown for clarity.

The arrangement of the actuators 500 has the advantage that only a pair of motors, one for each actuator 500, is necessary to accomplish the necessary tilting of the platform. FIGS. 4 and 11A show the table in a level position. Lateral tilt of the table as shown in FIGS. 11B and 11C is achieved by extending one of the actuators without extending the other actuator (or by extending the other actuator by a shorter distance). The actuators may be simultaneously lengthened or shortened for trendelenburg and reverse trendelenburg positioning. See FIG. 11D. Whereas prior art tables require a pair of motors for lateral tilt, a separate pair for trendelenburg motions, and an additional motor for elevating the table, a table in accordance with embodiments described herein needs only three motors, one to raise and lower the table and one for each actuator, where previous tables required five motors. The motors and actuators used can be any appropriate devices known or used in the art for driving the position of a moveable member, such as a spar of a medical table.

The table preferably includes a controller programmed to drive the actuators to place the patient in certain positions desirable for common procedures and a keypad 408 (FIG. 2) or instrument panel allowing for push-button movement of the table into desired orientations. For instance, a surgeon can activate a trendelenburg button or a left-tilt or right-tilt button to cause the software in the table to drive the actuators accordingly. The motion of the actuators 500 can be controlled through hardware or software, or a combination thereof. The surgeon or assistant can provide input through an appropriate input device, such as a joystick, a series of control buttons, or through voice activation. The table also can have return to zero functionality.

Figure 5A:
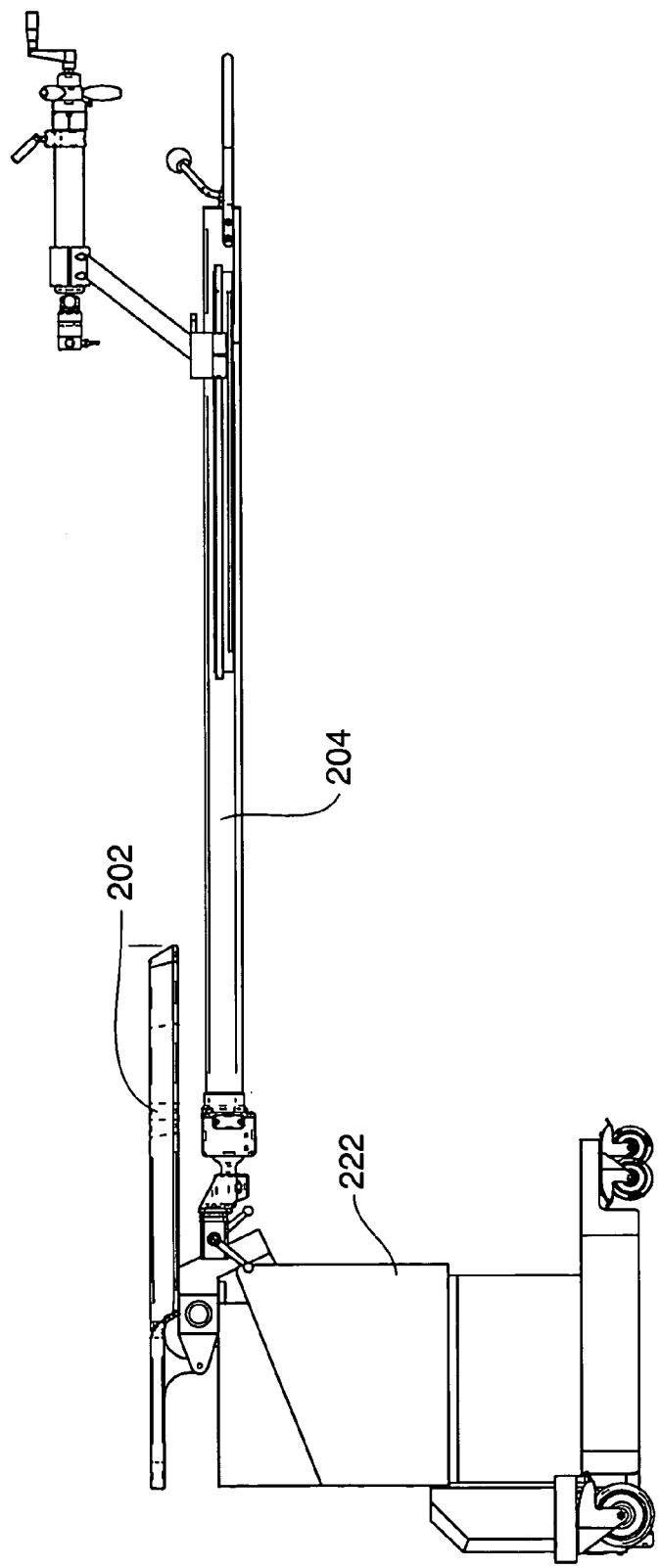
FIGS. 5A and 5B are side elevation views of the medical table of FIG. 2 with the table top in the level and the trendelenburg position, respectively.
Figure 5B:
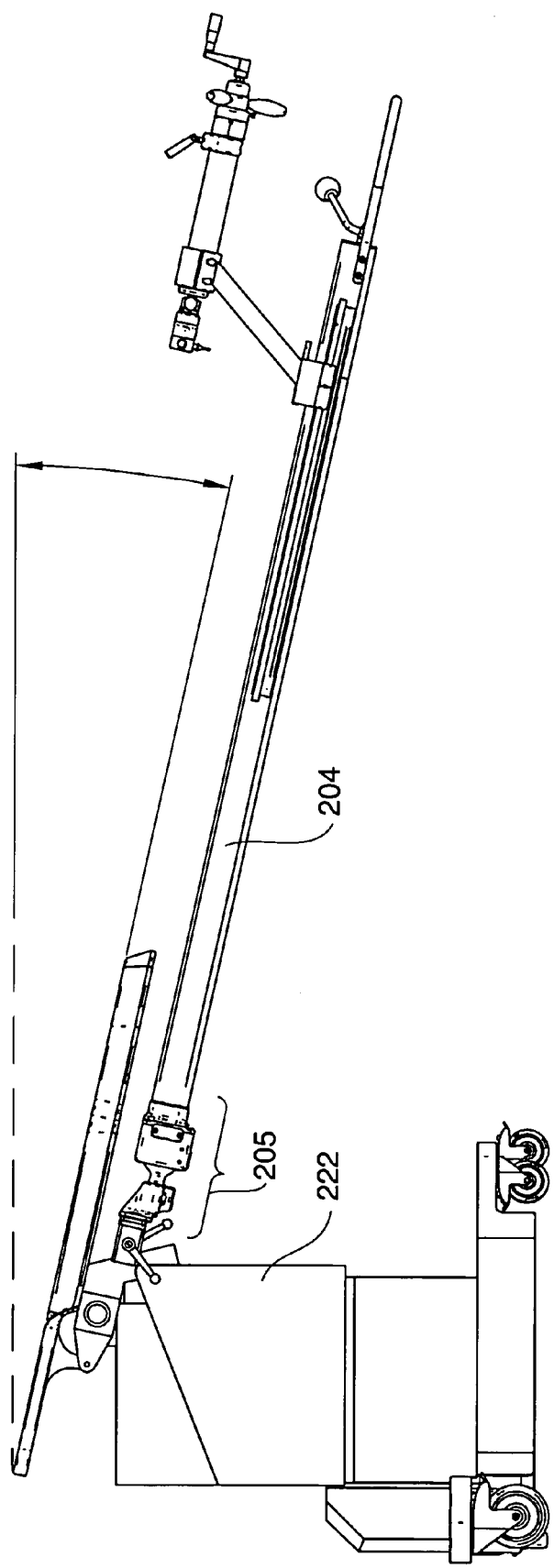
Figure 5C:
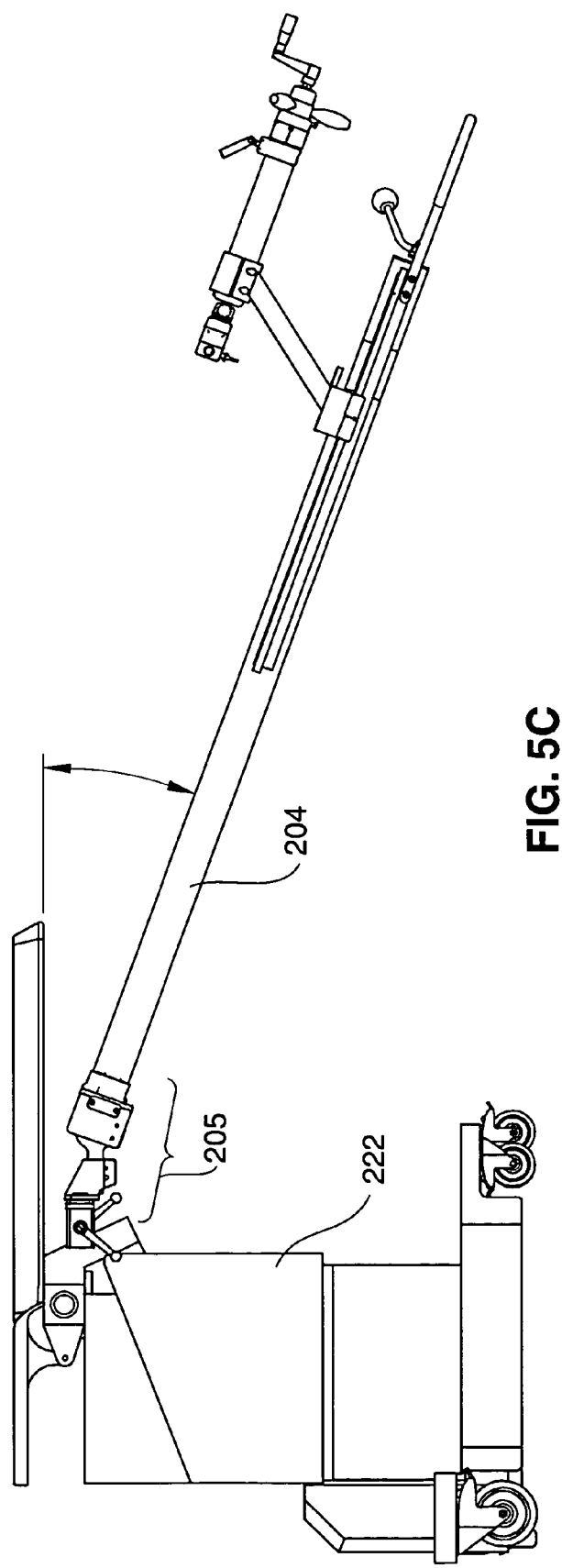
FIG. 5C is a side elevation view similar to FIG. 5B but shows the table top level with the leg spar in an angled position.
Figure 5D:
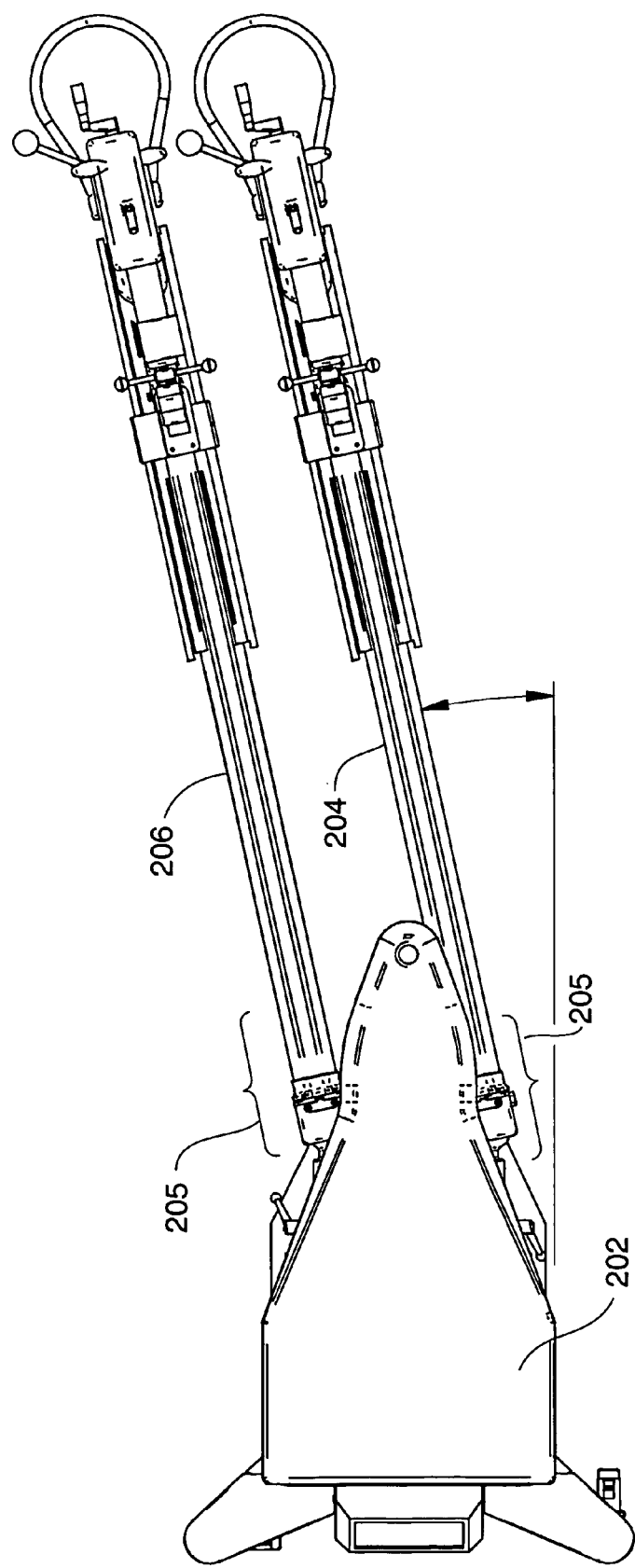
FIG. 5D is a top plan view of the medical table of FIG. 2, showing the leg spars angled to the left.

FIGS. 5A through 5D illustrate examples of positions of the platform 202 and the spars 204, 206 relative to the base 222. For example, table may be positioned with both the platform 202 and spars 204 parallel to the ground as shown in FIG. 5A, or the actuators 500 (FIG. 4) may be used to place the table in a trendelenburg position, with both the platform and spars at the same angle relative to the ground as shown in FIG. 5B. Regardless of the position of the platform 202, the spar angle relative to the ground may be adjusted separately from the platform angle 202 using the ball joint 205 as discussed above and as shown in FIG. 5C. Moreover, the ball joint 205 may be adjusted to abduct and/or adduct the spar positions as shown in FIG. 5D, or to rotate the spars about their longitudinal axes.

Figure 6:
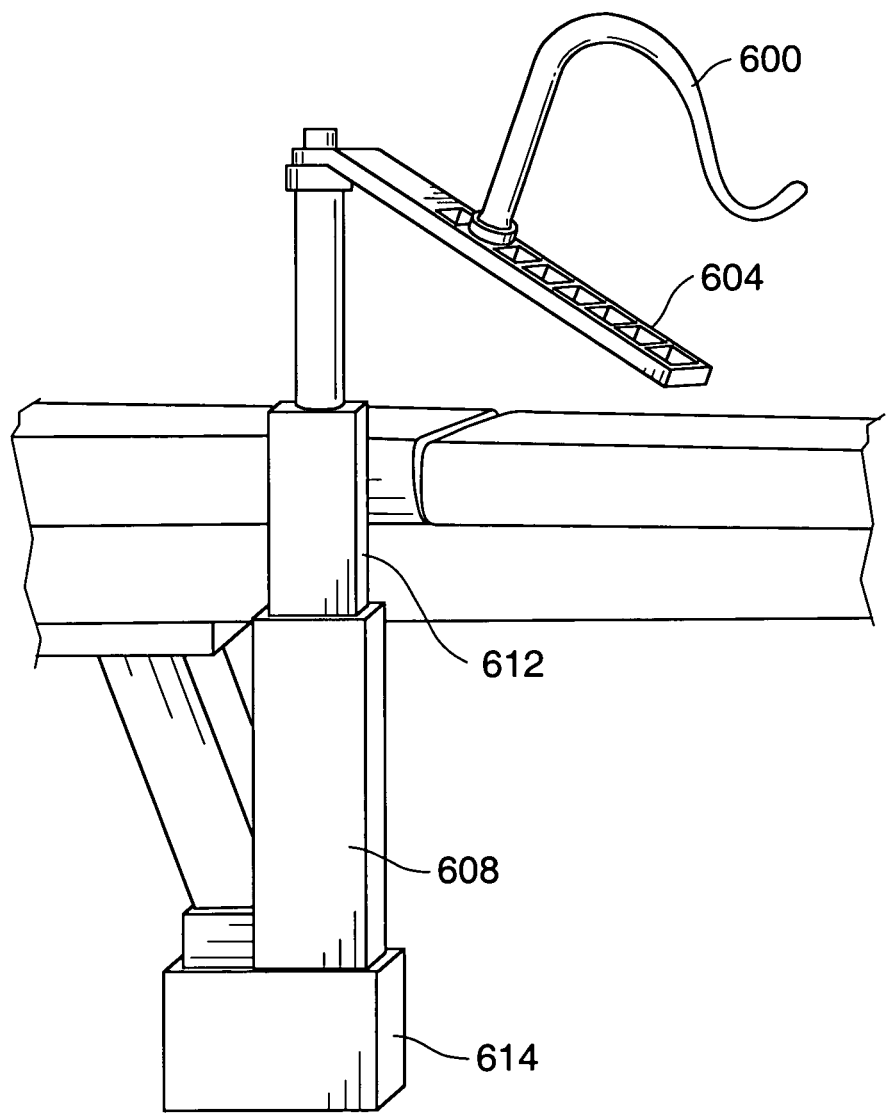
FIG. 6 is a perspective view of a portion of the medical table of FIG. 2 showing the detail of the femoral support hook.

FIGS. 2 and 6 illustrates a femoral support that can be used in accordance with the various embodiments. For example, a femoral support hook 600, 602 can be positioned on either side of the table 200 for supporting a respective femur. The hooks can be attached via an angled bracket 604 to an appropriate vertical positioning system or power lift, such as a motorized jack 608. Such a surgeon-controlled femoral power lift can enable hyperextension of the hip for improved surgical access. Proper placement allows the surgeon to effect hip replacement without the femur obstructing access to the acetabulum of the hip. The vertical positioning system can include a base portion designed to attach to the table, or to be fixedly positioned with relation to the table. Although a manual jack of the type described in connection with FIG. 1 may also be used, an advantage to using a motorized jack is that the surgeon can control the jack directly, such as through use of a remote control device, which can avoid any potential communication problems between the surgeon and an assistant turning a crank for a jack in previous systems.

Motorized jacks, which can be controlled by the surgeon through a base control unit, remote control unit, or foot pedal, can be used to raise and lower the appropriate femoral support hook. Each angled bracket 604 can be rotated relative to the respective jack 608 such that the surgeon performing the surgery can rotate the hook into and out of position, providing complete control of the positioning of the support relative to the femur. The motorized jack and control mechanism can include any appropriate devices known or used in the art for imparting a controlled amount of linear motion. As seen in the embodiment of FIG. 6, the jack can include a telescoping member 612 controlled by a rotary drive motor 614. In alternative embodiments, the position of the hook in the bracket and/or the rotation of the bracket can be accomplished through sliding mechanisms, or can be automated through use of a motorized device. These adjustments then could be accomplished by the appropriate control mechanism available to the surgeon and/or assistant.

While the movement of the hook or support mechanism can be automated, such as through computer control with appropriate force feedback technology, it still can be desirable (and in some cases necessary) for a surgeon to hold and feel the hook as it is being positioned, in order to ensure proper placement and prevent injury. Automation can be difficult, as each patient can have a unique amount of muscle tension, as well as a different weight and size. Having the surgeon hold the hook can lower the likelihood of fracturing the femur. Further, every portion of the table that is motorized has to have redundancy for power failures, etc., which increases the complexity and hence the cost of the table. Gearboxes with cranks can be used where appropriate to lower or adjust motorized components.

In operation, the surgeon can place a base portion of the support hook 600 into an appropriate opening on the angled bracket 604. The bracket has a plurality of openings for receiving the base portion, in order to position the receiving end of the hook at an appropriate distance from the femur to be supported. At the proper time after an incision is made in the patient, the hook 600 on the appropriate side can be swung into position in the wound at the hip region of the patient, and can be positioned to support the femur. The surgeon (or an assistant) then can cause the motorized jack 608 to properly angle and support the femur, by operating a foot pedal or control mechanism as discussed above, such that the surgeon can gain unrestricted access to the acetabulum and other portions of the hip in order to accomplish an artificial hip replacement for the patient.

As discussed above, it is necessary to maintain traction during movement of the spars (and hence the legs of the patient), due to the offset and non-concentric nature of the ball joint of the table and the hips of the patient. One way to accomplish this is to use a gear box positioned between a spar and a respective traction system, with the gear ratio set such that an amount of movement of the spar will adjust the position of the traction system, laterally along the spar, in order to maintain an appropriate amount of traction. Traction also can be maintained automatically, such as through computer control using a motorized device. An enclosed gearbox can eliminate pinch points in previous designs.

Figure 7:
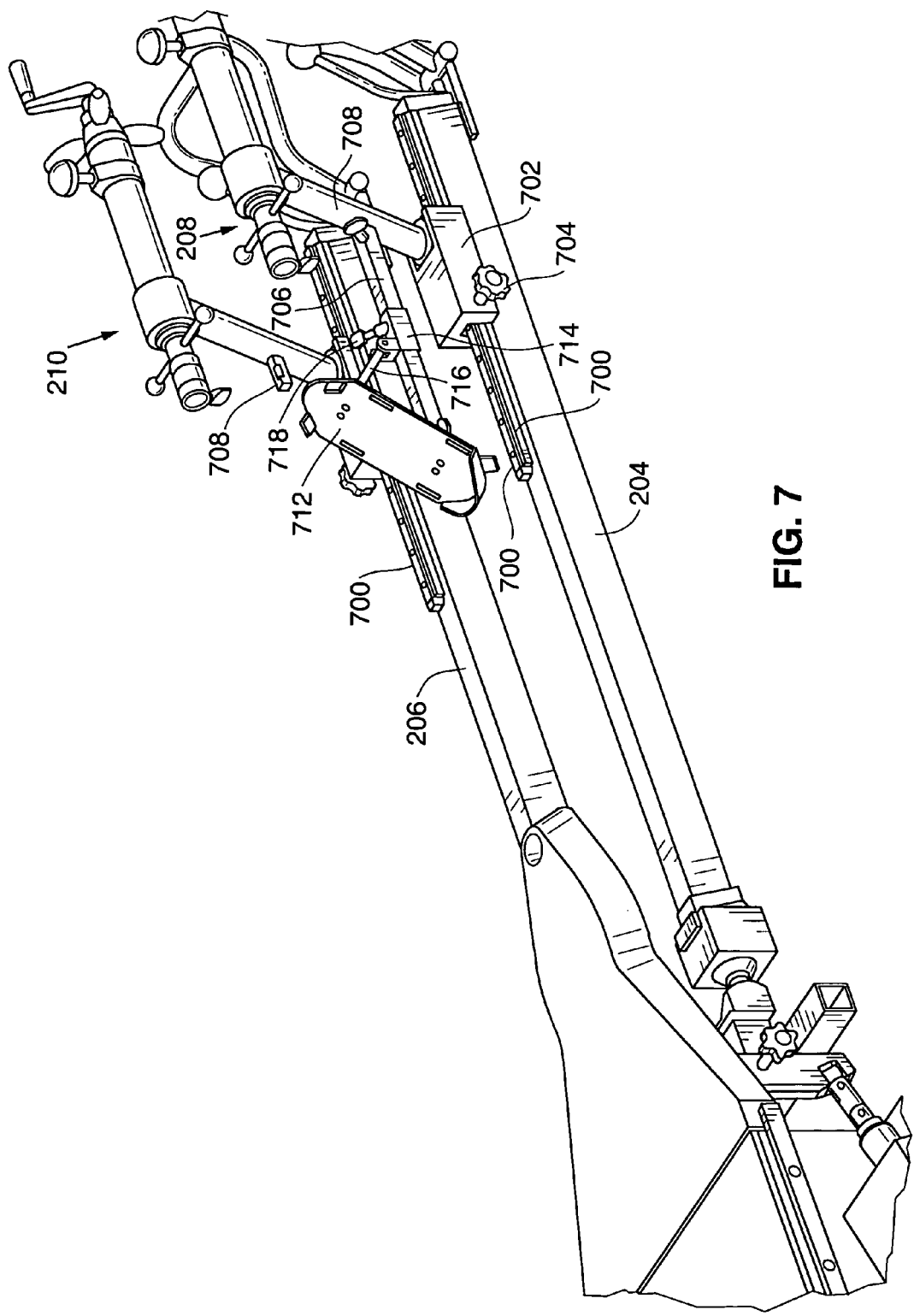
FIG. 7 is a perspective view of the spars of the medical table of FIG. 2.

A more simplistic and lightweight approach is shown in FIG. 7. In this approach, each spar 204, 206 includes a slider mechanism, which can consist of a rail 700 and a sliding mechanism or carriage 702 supporting a corresponding one of the traction systems 208, 210. As discussed in connection with FIG. 3, a traction boot 216 (not shown in FIG. 7) is mounted to the corresponding traction system. The carriage 702 can include a releasing mechanism 704 that can be used to releasably fasten the sliding mechanism in place along the rail, such that a loosening of the releasing mechanism allows the traction system to slide longitudinally along the spar as the spar is moved. Once the spar is in position, the releasing mechanism can be tightened in order to hold the traction system in place. Traction then can be adjusted by the traction adjustment mechanism as necessary. In one embodiment, a crank at the end of the spar is used to adjust traction. This is an advantage over previous tables as it is not necessary to go under the drape to change position.

Tables in accordance with the various embodiments table also can be equipped with a fully functional knee flexion system to accommodate knee procedures including total knee replacement. One such knee positioning attachment 706 is shown in FIG. 7, which is capable of positioning the leg of a patient as shown in FIG. 3 (see the right leg in FIG. 3). The knee positioning attachment can be an elongate rail connected to a receiving member 708 on the associated traction system 208, 210. The knee positioning mechanism includes a foot plate 712 for receiving and supporting a foot of the patient. The foot plate is connected via a support member 716 to a slider assembly 714. By releasing a tension knob 718 of the slider assembly 714, the slider assembly can be moved laterally along the rail of the knee positioning attachment in order to adjust an angle and position of the foot. Adjustments to the position of the foot can be used, in combination with the traction system, to control the bend angle of the knee of the patient. As discussed above, adjustments may be needed in order to provide proper access and alignment during knee surgery. Although a slider assembly with a tension knob is discussed, it should be understood that there are a number of other mechanisms and devices for adjusting a position and orientation of the foot of a patient that could be used within the scope of the various embodiments.

There are a number of advantages to such a knee positioning mechanism relative to devices of the prior art. The ability to move and lock above the surgical drape provides the ability to quickly and easily change knee flexion angle in a sterile environment. The mechanism can be made of a material such as stainless steel that can be steam sterilized or autoclaved on site. The boots used in previous tables were not (easily) sterilizable. The attachment also can simply plug onto an existing table. Such an attachment allows for easy adjustment to control the knee angle to get everything lined up as necessary. In order to remove portions of tibia and femur, it may be necessary to reposition the knee several times during surgery. Thus, the slide feature becomes an important working mechanism. Some existing tables use a foot plate on a general surgical table, which uses a bracket that provides discrete foot plate positions. A post in these tables can be lifted and put in different notches, which is more difficult (requires lifting the leg), provides fewer alignment options, and increases the risk of injury to the patient. The knee adjustment mechanism in various embodiments herein also can be motorized, and can be automated as necessary. The knee adjustment mechanism also can provide rotational control, allowing for discrete movement in any of three planes without disturbing the position in the other two planes.

Figure 8:
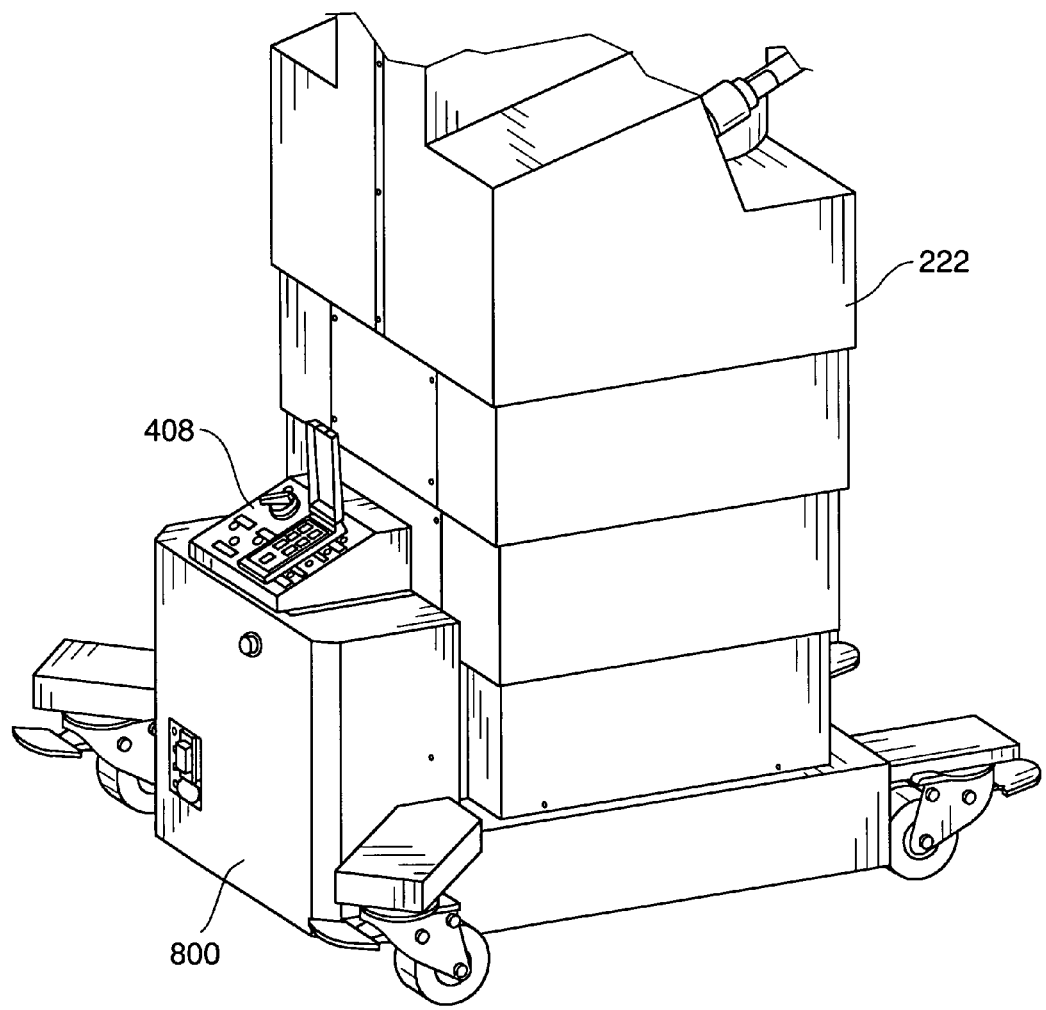
FIG. 8 is a perspective view of the pedestal of the medical table of FIG. 2.
Figure 9:
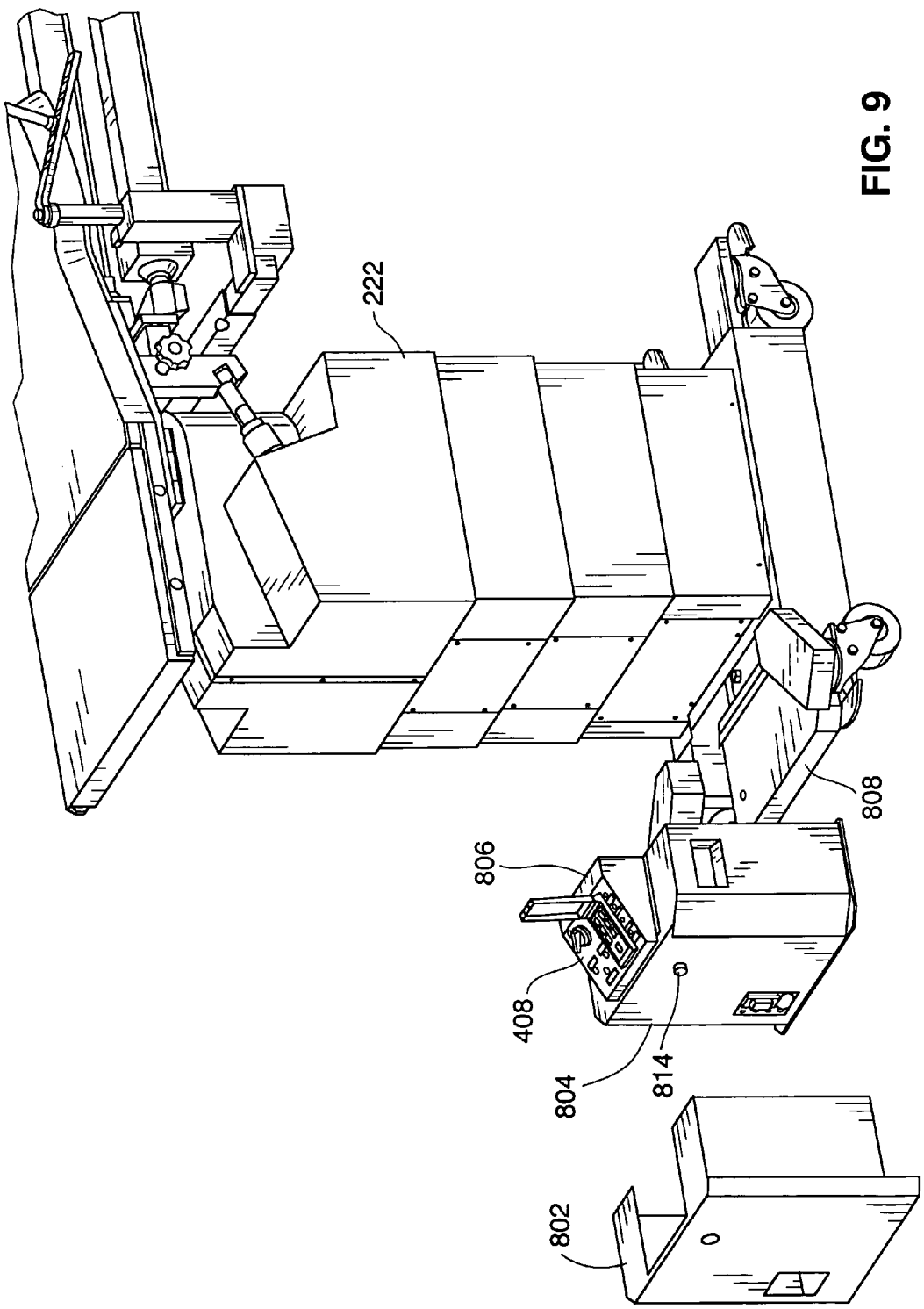
FIG. 9 is a perspective view similar to FIG. 8, showing the control module and cover piece separated from the pedestal.
Figure 10:
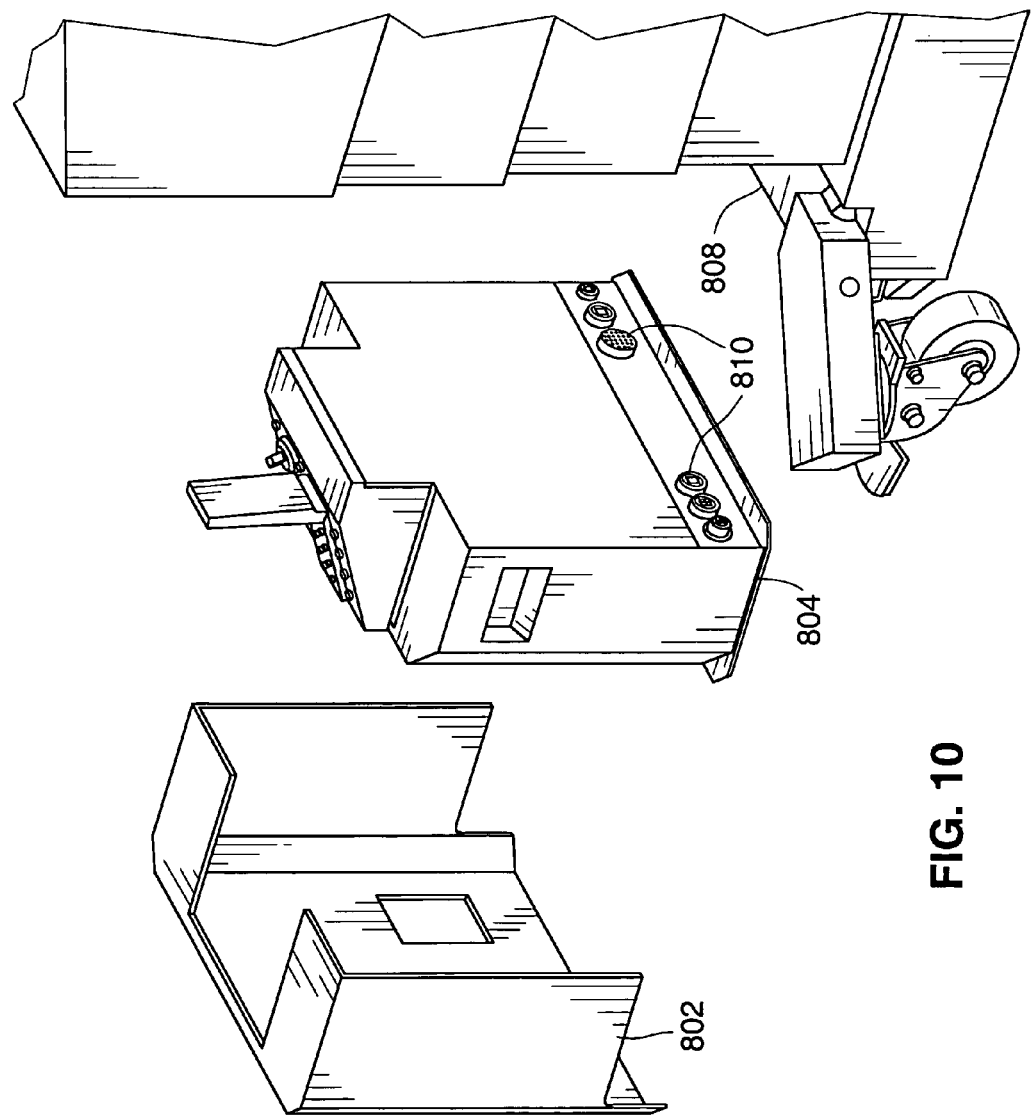
FIG. 10 is a perspective view of the pedestal showing the control module and cover piece separated from the pedestal.

The various embodiments described herein also can include a removeable control module 800 as shown in FIGS. 8-10. The control module 800 can be attached to the base 222 of the table, by any appropriate device such as a retaining screw 814. The control module can include a cover piece 802 for protecting the internal components of the control module 800. The control module also can include a replaceable main portion 804, which can include any appropriate power supply components, control circuitry and circuit boards, processors, memory, media devices, or other appropriate components that can be used with a medical table for control and/or operation. The module can include power components allowing for AC or battery operation. The control module also can include a control panel 408/806, which can be part of the replaceable main portion 804, can be attached to but removable from the base portion 222, or can be permanently fixed to the base. The base portion can include receiving components 808 for supporting the control module 800. In one embodiment, the control panel and main portion can be separately replaced. The replaceable main portion can include any appropriate ports or connectors 810 necessary to connect the components of the control module to the appropriate components of the table. This design is advantageous because a single module can simply be unplugged and replaced in order to fix problems with power supplies, circuitry, software, etc. In prior systems, it was necessary to remove panels, troubleshoot, and unhook individual components, which can take a substantial amount of time and is undesirable during a surgical procedure. A removable control module allows for quick and easy replacement without the need for troubleshooting during the procedure. The control module also can include troubleshooting hardware and/or software, and can include a continuous monitoring system that can alert a user, such as through LEDs or a display panel, as to the need for service or current operating conditions. The software also can provide complex movement options that can be selected by the surgeon, and can provide preventative modules in combination with sensors or feedback devices to prevent injury due to excessive movement or force caused by operation of the table.

It should be recognized that a number of variations of the above-identified embodiments will be obvious to one of ordinary skill in the art in view of the foregoing description. Accordingly, the invention is not to be limited by those specific embodiments and methods of the present invention shown and described herein. Rather, the scope of the invention is to be defined by the following claims and their equivalents.

Any and all patents, patent applications and printed publications referred to above, including those relied upon for purposes of priority, are fully incorporated by reference.

What is claimed is:

1. A surgical table apparatus for an arthroplasty procedure utilizing an incision in a patient creating a wound at the hip region of the patient, comprising:
   a. a platform for supporting a patient,
   b. a base supporting said platform and allowing for adjustment of a position of said platform;
   c. a control mechanism said control mechanism including at least one of power components and control components for controlling the position of said platform; and
   d. a femoral support device associated with said platform, said femoral support device comprising a femoral support hook to contact the femur and a positioning mechanism configured and operable to adjust the placement of said femoral support hook of said femoral support device, into position in the wound at the hip region of the patient, said positioning mechanism further comprising a motorized positioning mechanism.

2. The apparatus of claim 1 which further comprises a pair of spars rotatably connected to one of the platform and the base, each spar operable to control a position of a leg of the patient.

3. The apparatus of claim 2 which further comprises a traction system coupled to one of said spars, the traction system attachable to a leg of a patient for maintaining traction on the leg, said traction system being slidable relative to a longitudinal axis of said spar during rotational movement of said spar relative to said base.

4. The apparatus of claim 3 in which said traction system includes a locking member for locking the longitudinal position of the traction system on said one spar.

5. The apparatus of claim 2 which further comprises a knee positioning attachment detachably coupled to one of said traction system, said spars knee positioning attachment operable to engage a foot of the patient and having a moveable support member for adjusting an angle of a knee in the respective leg of the patient.

6. The apparatus of claim 1 in which said base supporting said platform includes at least one motor for controlling a position of the platform.

7. The apparatus of claim 1 which further comprises a first motor operable to adjust a vertical position of said platform; and second and third motors, each operatively associated with an actuator, each of said second and third motors operable to control both lateral tilt and trendelenburg tilt of said platform.

8. The apparatus of claim 1 which further comprises a remote control device for activating said control mechanism.

9. The apparatus of claim 1 in which said remote control device comprises a foot pedal.

10. The apparatus of claim 1 which further comprises a jack linked to said femoral hook.

11. The apparatus of claim 10 in which said jack further includes a telescoping member and a motor operating said telescoping member.

* * * * *